United States Patent [19]

Harris

[11] Patent Number: 4,606,862
[45] Date of Patent: Aug. 19, 1986

[54] AMIDES OF N-(3-(1-CHLORO-2-NITROETHENYLTHIO)-PROPANE)

[75] Inventor: Martin Harris, Sittingbourne, United Kingdom

[73] Assignee: Shell Oil Company, Houston, Tex.

[21] Appl. No.: 714,318

[22] Filed: Mar. 21, 1985

Related U.S. Application Data

[62] Division of Ser. No. 641,618, Aug. 17, 1984, Pat. No. 4,531,002.

[30] Foreign Application Priority Data

Aug. 26, 1983 [DE] Fed. Rep. of Germany ....... 8323057
Aug. 26, 1983 [GB] United Kingdom ................. 8323059
Aug. 26, 1983 [GB] United Kingdom ................. 8323060
Aug. 26, 1983 [GB] United Kingdom ................. 8323061

[51] Int. Cl.[4] ..................... C08H 3/00; C07C 153/00; C07F 9/24
[52] U.S. Cl. .................. 260/402.5; 558/169; 558/236; 560/137; 562/555; 564/59; 564/79; 564/90; 564/98; 564/102; 564/186; 564/209; 564/215
[58] Field of Search ............... 260/948, 455 A, 402.5; 568/56; 560/137, 148; 564/59, 102, 186, 209, 215, 79, 90, 98; 558/169, 175, 236

[56] References Cited

U.S. PATENT DOCUMENTS 3,363,001 1/1968 Schlechter et al. ................... 568/56

FOREIGN PATENT DOCUMENTS 134615 3/1985 European Pat. Off. .
135956 4/1985 European Pat. Off. .
753810 8/1956 United Kingdom ................. 568/56

*Primary Examiner*—Anton H. Satto

[57] ABSTRACT

A process for preparing insecticidal N-acyl-tetrahydro-2-nitromethylene-2H-1,3-thiazines, intermediates involved therein and certain of the products.

5 Claims, No Drawings

AMIDES OF N-(3-(1-CHLORO-2-NITROETHENYLTHIO)PROPANE)

This is a division of application Ser. No. 641,618, filed Aug. 17, 1984, now U.S. Pat. No. 4,531,002.

BACKGROUND TO THE INVENTION

U.S. Pat. No. 4,065,605 discloses tetrahydro-2-nitromethylene-2H-1,3-thiazine

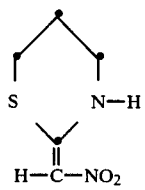

(A)

and certain N-substituted congeners, having useful insecticidal properties. German patent specification No. 3,310,744-A and U.S. patent application Ser. No. 578,142 disclose insecticidal N-acyl derivatives of Compound A, having improved physical properties. Hitherto, all of such N-acyl derivatives have been prepared by treating the N-unsubstituted compounds with suitable reagents. However, attempts to prepare certain N-acyl derivatives by direct acylation have failed. Moreover, synthesis of Compound A by the method disclosed in U.S. Pat. No. 4,065,605 involves the use of hazardous intermediates, so that a route to the N-acyl derivatives that does not involve Compound A is desirable.

DESCRIPTION OF THE INVENTION

It has now been found that these N-acyl derivatives can be prepared by a process that avoids Compound A and its congeners. Further, it has been found that this new process effects the preparation of N-acyl derivatives that were not accessible by the known route.

Accordingly, this invention provides a process for preparing a compound of the formula

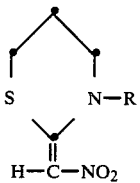

(I)

wherein R is an acyl moiety derived from an organic acid, which comprises treating a compound of the formula

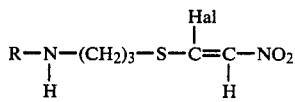

(II)

wherein Hal is a halogen atom, with a base, in the presence of an inert solvent.

In the compounds of formulae I and II, R represents an optionally substituted acyl moiety of up to 20 carbon atoms derived from an organic acid. The organic acid may be a carboxylic acid, or a mono- or di-thio-analog thereof; it may be a carbamic or carbonic acid; it may be a sulfonic or aminosulfonic acid; or it may be a phosphorus-containing acid. Particular examples of acyl moieties derived from such acids are optionally substituted: formyl, alkanoyl, alkenoyl, alkynoyl, benzoyl, carbamoyl, oxaloyl, alkoxycarbonyl, phenoxycarbonyl, phenalkoxycarbonyl, alkylthiocarbonyl, phenylthiocarbonyl, alkylthio-thiocarbonyl, phenylthio-thiocarbonyl, alkylsulfonyl, phenylsulfonyl, alkylaminosulfonyl, phenylaminosulfonyl, or phosphorus-containing acyl of the formula

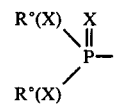

wherein each of R° independently is an optionally substituted alkyl or phenyl moiety, and each X independently is an oxygen or sulfur atom.

The optional substituent(s) which may be present in the acyl moiety are preferably selected from fluorine, chlorine, bromine and iodine; nitro; cyano; alkyl, alkoxy, alkylthio, alkenyl, and alkynyl preferably of up to 6 carbon atoms; and phenyl, phenoxy or phenylthio, optionally substituted with one or more moieties selected from fluorine, chlorine, bromine, iodine, alkyl of 1 to 4 carbon atoms, nitro and cyano.

The process of the invention is particularly useful for preparing compounds of Formula I in which R is alkanoyl (e.g. containing 1 to 11 carbon atoms), haloalkanoyl (e.g. containing 2 to 11 carbon atoms and 1 to 5 chlorine, fluorine and/or bromine atoms), phenylsulfonyl, alkylsulfonyl (e.g. alkylsulfonyl containing 1 to 10 carbon atoms), (alkyl—O)$_2$P(O)— (e.g. where each alkyl moiety contains 1 to 4 carbon atoms), (alkyl—O)$_2$P(-S)— (e.g. where each alkyl moiety contains 1 to 4 carbon atoms, (phenyl—O)$_2$P(O)—, dialkylcarbamoyl (e.g. where each alkyl contains 1 to 4 carbon atoms), alkoxycarbonyl (e.g. containing 2 to 11 carbon atoms), or alkylthiocarbonyl (e.g. containing 2 to 11 carbon atoms), wherein each of these can bear methyl, nitro, chlorine, fluorine or bromine as substituents.

Suitable bases for use in the process of the invention for preparing compounds of Formula I are sodium or potassium hydride, sodium or potassium alkoxide in which the alkyl group contains 1 to 8 carbon atoms and is preferably branched, e.g. a tertiary alkyl group, and sodium, potassium or lithium amides or dialkylamides wherein each alkyl group contains 1 to 8 carbon atoms, e.g. sodamide and sodium di-isopropylamide.

Any suitable solvent may be used, for example, tertiary alcohols, such as t-butyl alcohol, ethers, such as diethyl ether, tetrahydrofuran and dimethoxyethane, ketones, such as acetone, nitrogenous solvents, such as dimethylformamide, hydrocarbons, such as benzene, xylene and toluene, and sulfur-containing solvents, such as dimethyl sulfoxide.

The reaction may proceed at room temperature but in general it can take place at temperatures between −30° C. and +50° C., suitably between −20° and +30° C.

The molar ratio of the reactants is unimportant, e.g. the molar ratio of base to amide can be in the range 1:2 to 2:1, but generally speaking it is preferred to have the basic reactant in excess, i.e. the molar ratio is preferably in the range 1:1 to 2:1.

The N-substituted-S-substituted aminothiols of Formula II are novel compounds, and form a further aspect of the invention. They may be prepared by a process which comprises treating an aminopropanethiol of the formula

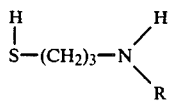

with a halonitroethylene of the formula

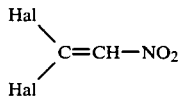

wherein Hal is a halogen atom, in the presence of a base, for example, a hydroxide, carbonate, bicarbonate or acetate of an alkali or alkaline earth metal or of ammonium, and in the presence of an inert solvent. Conveniently, the base is an alkali metal hydroxide such as sodium or potassium hydroxide. The inert solvent can, for example, be any one of the solvents referred to hereinbefore.

It is generally preferred to isolate the amide of Formula II before subjecting it to the action of a base to form the compound of Formula I. However, isolation of the intermediate II is not essential and the compound of Formula I can be made directly by reacting the aminothiol III with the halonitroethylene IV in the presence of base.

The aminothiol compounds of Formula III may be prepared by N-acylation of the corresponding unsubstituted aminothiol, and this forms a further aspect of the invention. Thus, such N-substituted-aminothiols of Formula III can be prepared by treating an aminothiol of the formula

with an acylating agent of the formula

R—Hal or R—O—R in the presence of an inert solvent and, in the case of R—Hal, in the presence of a hydrogen halide acceptor, for example, a base such as tertiary amine.

In some cases the reaction of the acylating agent with the aminothiol V results in the formation of a disulfide of the general formula

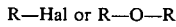

The required N-acyl-thiol can be obtained by cleavage of the disulfide VI using a reducing agent, for example, sodium borohydride, zinc and acetic acid, tin and hydrochloric acid, sodium with xylene, ether or ammonia, and triphenylphosphine.

Any solvent which is a convenient medium in which to carry out the reaction is suitable: for example, alcohols such as methanol, ethanol and butanol, and the solvents described hereinbefore to be useful in the preparation of compounds of Formula I.

The reaction may proceed at room temperature but in general it is desirable to conduct the reaction at temperatures between −30° and +50° C., suitably between −20° and +30° C.

Practice of the method of the invention in particular instances is illustrated in the following Examples. Examples 1 to 22 illustrate the synthesis of the novel N-substituted-S-substituted-aminothiols (II) and their precursors, while Examples 23 to 29 illustrate conversion into compounds of Formula I. In each case, unless otherwise stated, the identity of the product, and of any intermediate involved, was confirmed by appropriate chemical and spectral analyses.

EXAMPLE 1

N-(3-Mercaptopropyl)acetamide (1)

Sodium methoxide (1 g of sodium in 25 ml of methanol) was added to 5 g of the hydrochloride salt of 3-aminopropanethiol (1A), and the mixture was allowed to cool. Then 5 g of acetic anhydride was added and the mixture was stirred for 30 minutes. Ether was added, the resulting mixture was filtered and the filtrate was evaporated to dryness (90° C.). The residue was extracted with methylene chloride, and the extract was evaporated to dryness. Purification of the residue on an alumina column gave 1, as a oil.

EXAMPLE 2

1,1-Dimethyl-3-(mercaptopropyl)urea (2)

5 g of 1A was treated with sodium methoxide as described in Example 1. The methanol was evaporated under reduced pressure. 4 g of dimethylcarbamoyl chloride, 6 g of triethylamine and 30 ml of methylene chloride were added over 10 minutes at 0° C. under nitrogen. The resulting mixture was held overnight at room temperature, then was poured into a 2% hydrochloric acid solution saturated with sodium chloride. Purification of the organic phase over silica gel gave 2.

EXAMPLE 3

N-(3-Mercaptopropyl)benzenesulfonamide (3)

5 g of 1A was treated with sodium methoxide as described in Example 1. The solvent was evaporated. The residue was mixed with 60 ml of methylene chloride and 6 g of triethylamine, then a solution of 7 g of phenylsulfonyl chloride in 40 ml of methylene chloride was added drop-by-drop over 30 minutes, at 0° C. The resulting mixture was held at room temperature for 20 minutes, and the solid product was separated, washed with 2% hydrochloric acid and triturated with diethyl ether to give bis(3-(phenylsulfonylamino)propyl)disulfide (3A).

3.1 g of 3A was treated with a mixture of 2.5 g of triphenylphosphine, 2.5 g of water, 50 ml of methanol and 10 drops of 10% hydrochloric acid. The resulting mixture was refluxed for 11 hours, then most of the solvent was evaporated and the residue was extracted with methylene chloride. The extract was washed with water, the solvent was evaporated and the residue was chromatographed over silica gel to give 3.

EXAMPLE 4

N-(3-Mercaptopropyl)benzamide (4) was prepared from 1A and benzoyl chloride by the procedures described in Examples 1–3.

EXAMPLES 5–12

The following further individual species of these aminothiols, identified in terms of the moiety, R, formula III, were prepared by the procedures described in Examples 1–4. None of the species was isolated, and in each case the crude product was used further in the process of the invention.

TABLE I

| Example No. | Compound No. | R |
|---|---|---|
| 5 | 5 | $CF_3C(O)-$ |
| 6 | 6 | $(C_2H_5O)_2P(O)-$ |
| 7 | 7 | $(CH_3)_3C(O)-$ |
| 8 | 8 | $(C_2H_5O)_2P(S)-$ |
| 9 | 9 | $(CH_3)_2CHSO_2-$ |
| 10 | 10 | $(CH_3)_3CHC(O)-$ |
| 11 | 11 | $C_2H_5SC(O)-$ |
| 12 | 12 | $(C_6H_5O)_2P(O)-$ |

EXAMPLE 13

N-(3-(1-Chloro-2-nitroethenylthio)propyl)acetamide (13)

A solution of 0.12 g of sodium hydroxide in 5 ml of methanol was added over 10 minutes to a solution of 0.40 g of 1 in 5 ml of methanol. Then a solution of 0.95 g of 1,1-dichloro-2-nitroethene (13A) in 5 ml of methanol was added over 20 minutes, at 0° C. The mixture then was stirred for 20 minutes and poured into 2% hydrochloric acid saturated with sodium chloride. The resulting mixture was extracted with methylene chloride, the solvent was evaporated and the residue was purified over silica gel to give 13, as an oil.

EXAMPLE 14

N-(3-(1-Chloro-2-nitroethenylthio)propyl)benzenesulfonamide (14)

A solution of 0.08 g of sodium hydroxide in 3 ml of methanol was added drop-by-drop over 5 minutes to a solution of 0.23 g of 3 in 5 ml of methanol. The resulting mixture was added drop-by-drop over 20 minutes to a solution of 0.28 g of 13A in 6 ml of methanol at 0° C. The mixture was held at 0° C. for 30 minutes, then poured into 2% hydrochloric acid saturated with sodium chloride. The resulting mixture was extracted with methylene chloride, the solvent was evaporated from the extract and the residue was chromatographed over silica gel to give 14, as a solid, m.p.: 105°–106° C.

EXAMPLE 15

N-(3-(1-Chloro-2-nitroethenylthio)propyl)benzamide (15)

15 was prepared from 4 and 13A by the procedures described in Examples 13 and 14.

EXAMPLES 16–25

The following further individual species of these N-substituted-S-substituted aminothiols, identified in terms of the moiety, R, Formula II, and the precursor aminothiol, were prepared from 13A by the procedures described in Examples 13 and 14.

TABLE II

| Example No. | Compound No. | R | Aminothiol | Physical State |
|---|---|---|---|---|
| 16 | 16 | $CF_3C(O)-$ | 5 | oil |
| 17 | 17 | $(CH_3)_3C(O)-$ | 7 | not isolated |
| 18 | 18 | $(C_2H_5O)_2P(S)-$ | 6 | oil |
| 19 | 19 | $(C_6H_5O)_2P(O)-$ | 12 | oil |
| 20 | 20 | $(CH_3)_2NC(O)-$ | 2 | oil |
| 21 | 21 | $4\text{-}BrC_6H_4SO_2-$ | | solid, m.p.: 96–97° C. |
| 22 | 22 | $(CH_3)_2NSO_2-$ | | oil |
| 23 | 23 | $HC(O)-$ | | not isolated |

EXAMPLE 24

N-Benzoyl-tetrahydro-2-nitromethylene-2H-1,3-thiazine (24)

A solution of 0.10 g of potassium t-butoxide in 3 ml of t-butanol was added drop-by-drop over 5 minutes to a solution of 0.23 g of 15 in 10 ml of t-butanol under nitrogen, at room temperature. After 40 minutes, the mixture was poured into 2% hydrochloric acid saturated with sodium chloride and the resulting mixture was extracted with methylene chloride. The solvent was purified over silica gel to give 24, as a solid, m.p.: 90°–92° C.

EXAMPLE 25

N-(Phenylsulfonyl)-tetrahydro-2-nitromethylene-2H-1,3-thiazine (25)

25 was prepared, as a solid, m.p.: 107° C., from 14, by the procedures described in Example 24.

25 also was prepared without isolating the intermediate (14), as follows:

0.22 g of potassium t-butoxide was added drop-by-drop over 10 minutes to a solution of 0.23 g of 3 in 5 ml of t-butanol, under nitrogen. The resulting mixture was added drop-by-drop over 20 minutes to 0.30 g of 13A. After 20 minutes at room temperature, the mixture was poured into 2% hydrochloric acid saturated with sodium chloride, the resulting mixture was extracted with methylene chloride, the solvent was evaporated from the extract and the residue was purified over silica gel, using methylene chloride as eluent, to give 25, m.p.: 106°–107° C.

EXAMPLE 26

N-(Diethoxyphosphinothioyl)-tetrahydro-2-nitromethylene-2H-1,3-thiazine (26)

26 was prepared, as an oil, from 8, by the procedures described in Example 24.

EXAMPLES 27–31

The following further individual species of the compounds of Formula I, identified in terms of the moiety, R, Formula I, and the precursor N-substituted-S-substituted aminothiol, were prepared according to the procedures described in Example 25.

TABLE III

| Example No. | Compound No. | R | Aminothiol | Melting Point (°C.) |
|---|---|---|---|---|
| 27 | 27 | $p\text{-}BrC_6H_4SO_2-$ | 20 | 96–97 |
| 28 | 28 | $(CH_3)_2NC(O)-$ | 19 | 104–106 |
| 29 | 29 | $(CH_3)_2NSO_2-$ | 21 | 92–93 |
| 30 | 30 | $HC(O)-$ | | 132 |
| 31 | 31 | $CH_3(O)-$ | 1 | 91–92.5 |

As already mentioned, compounds of Formula I are of interest as insecticides, exhibiting activity against such pests as the larval caterpillar or worm forms of insects, for examples, of the genus Spodoptera and of the genus Heliothis, and are particularly useful against pests found in rice crops. The compounds also exhibit acceptable stability towards light and oxidation.

Accordingly, the invention includes an insecticidal composition of Formula I together with a carrier.

Such a composition may contain a single compound or a mixture of several compounds of the invention. It is also envisaged that different isomers or mixtures of isomers may have different levels or spectra of activity and thus compositions may comprise individual isomers or mixtures of isomers. The invention further provides a method of combating insects at a locus infested, or liable to infestation, by insects, which comprises applying to the locus an insecticidally effective amount of compound or composition according to the present invention.

A carrier in a composition according to the invention is any material with which the active ingredient is formulated to facilitate application to the locus to be treated, which may, for example, be a plant, seed or soil, or to facilitate storage, transport or handling. A carrier may be a solid or a liquid, including a material which is normally gaseous but which has been compressed to form a liquid, and any of the carriers normally used in formulating pesticidal compositions may be used. Preferably, compositions according to the invention contain 0.5 to 95% by weight of active ingredient.

Suitable solid carriers include natural and synthetic clays and silicates, for example, natural silicas such as diatomaceous earths; magnesium silicates, for example, talcs; magnesium aluminum silicates, for example, attapulgites and vermiculites; aluminum silicates, for example, kaolinites, montormorillonites and micas; calcium carbonate; calcium sulfate; ammonium sulfate; synthetic hydrated silicon oxides and synthetic calcium or aluminum silicates; elements, for example, carbon and sulfur; natural and synthetic resins, for example, coumarone resins, polyvinyl chloride, and styrene polymers and copolymers; solid polychlorophenols; bitumen; waxes; and solid fertilizers, for example, superphosphates.

Suitable liquid carriers include water; alcohols, for example, isopropanol and glycols; ketones, for example, acetone, methyl ethyl ketone, methylisobutyl ketone and cyclohexanone; ethers; aromatic or araliphatic hydrocarbons, for example, benzene, toluene and xylene; petroleum fractions, for example, kerosene and light mineral oils; chlorinated hydrocarbons, for example, carbon tetrachloride, perchloroethylene and trichloroethane. Mixtures of different liquids are often suitable.

Agricultural compositions are often formulated and transported in a concentrated form which is subsequently diluted by the user before application. The presence of small amounts of a carrier which is a surface-active agent facilitates this process of dilution. Thus, preferably, at least one carrier in a composition according to the invention is a surface-active agent. For example, the composition may contain at least two carriers, at least one of which is surface-active agent.

A surface-active agent may be an emulsifying agent, a dispersing agent or a wetting agent; it may be nonionic or ionic. Examples of suitable surface-active agents include the sodium or calcium salts of polyacrylic acids and lignin sulfonic acids; the condensation of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohol or alkyl phenols, for example, p-octylphenol or p-octylcresol, with ethylene oxide and/or propylene oxide; sulfates or sulfonates of these condensation products; alkali or alkaline earth metal salts, preferably sodium salts, of sulfuric or sulfonic acid esters containing at least 10 carbon atoms in the molecule, for example, sodium lauryl sulfate, sodium secondary alkyl sulfates, sodium salts of sulfonated castor oil, and sodium alkylaryl sulfonates such as dodecylbenzene sulfonate; and polymers of ethylene oxide and copolymers of ethylene oxide and propylene oxide.

The composition of the invention may, for example, be formulated as a wettable powder, a dust, granules, a solution, an emulsifiable concentrate, an emulsion, a suspension concentrate or an aerosol. The composition may have controlled release properties.

Wettable powders usually contain 25, 50 or 75% of active ingredient and may contain, in addition to inert solid material, 3–10% of a dispersing agent, and, where necessary, 0–10%w of a stabilizer, a penetrant and/or a sticker. A dust is usually formulated as a dust concentrate having a composition similar to that of a wettable powder but without a dispersant, and is diluted in the field with further solid carrier to give a composition usually containing 0.5–10%w of active ingredient.

Granules usually have a size in the range of from 10 to 100 BS mesh (1.676–0.152 mm) and may be manufactured by agglomeration or impregnation techniques. Generally, granules will contain 0.5–75%w active ingredient and 0–10%w of additives, such as stabilizers, surfactants, slow release modifiers and binding agents.

Emulsifiable concentrates usually contain, in addition to a solvent, and, when necessary, co-solvent, 10–50% w/v active ingredients, 2–20% w/v emulsifier and 0–20% w/v of other additives, for example, a stabilizer, a penetrant and/or a corrosion inhibitor. A suspension concentrate is a stable, non-sedimenting, flowable product and usually contains 10–75%w active ingredient, 0.5–15% of dispersing agent, 0.1–10%w of suspending agent, for example, protective colloid and/or a thixotropic agent, and 0–10%w of other additives including, for example, a defoamer, a corrosion inhibitor, a stabilizer, a penetrant and/or a sticker, and as dispersant, water or an organic liquid in which the active ingredient is substantially insoluble; certain organic additives and/or inorganic salts may be dissolved in the dispersant to assist in preventing sedimentation or as antifreeze for water.

The aqueous dispersions and emulsions formed by diluting a wettable powder or an emulsifiable concentrate of the invention with water, also lie within the scope of the present invention. Such dispersions and emulsions may be of the water-in-oil or of the oil-in-water type, and may have a thick "mayonnaise"-like consistency.

A composition of the invention may also contain other ingredients, for example, one or more other compounds possessing pesticidal properties. Further insecticidal compounds may be included, particularly such compounds having a different mode or spectrum of activity.

The thermal stability of the compounds and compositions of the invention may be improved by the addition of stabilizing amounts, usually 10–100%w based on the compound of certain organo nitrogen compounds such as urea, dialkylureas, thiourea or guanidine salts or alkali metal salts of weak acids such as bicarbonates, acetates or benzoates.

Pesticidal Activity

The pesticidal activities of the compounds of the invention were assessed employing the following insect pests. The tests were all conducted under normal insectary conditions 23° C.±2° C. (fluctuating light and humidity).

Spodoptera littoralis (S.l.)

Second instar larvae were used in the tests. A 0.2% solution or suspension of each test compound in 16.7% acetone in water containing 0.04% Triton X-100 (Trade Mark) was sprayed onto a separate petri dish containing a nutritious diet on which the Spodoptera littoralis larvae had been reared. Controls were sprayed with a control solution of water, acetone and Triton X-100 (Trade Mark) in the same proportions.

When the spray deposit had dried each dish was infested with 10 2nd instar larvae. Mortality assessments were made 1 and 7 days after spraying and the percentage mortality was calculated.

Aedes aegypti (A.a.)

Early 4th instar larvae were used in the tests. Test solutions were made up to 3 ppm of active ingredient in water containing 0.04% Triton X-100 (Trade Mark); acetone was initially present to aid solution, but was subsequently allowed to evaporate off.

Ten early 4th instar larvae were placed in 100 ml of the test solution. After 48 hours, larval mortality (as a percentage) was recorded.

Any surviving larvae were then fed with a small quantity of animal feed pellets and the final percentage mortality of adults and pupae made when all the larvae had either pupated and turned into adults, or died.

The results of these tests are shown in Table IV in which the test species are identified by the initials noted above and the activity of each compound is expressed in terms of the percentage mortality:

A denotes 99–100% mortality
B denotes 50–80% mortality
C denotes 0–40% mortality

TABLE IV

| Compound No. | S.l. 24 hr | S.l. 7 day | A.a. 24 hr | A.a. Final |
|---|---|---|---|---|
| 23 | A | A | A | A |
| 24 | A | A | A | A |
| 25 | A | A | A | A |
| 26 | B | A | A | A |
| 27 | A | A | C | C |
| 28 | A | A | A | A |
| 29 | A | A | A | A |
| 30 | A | A | A | A |

I claim:
1. A compound of the formula

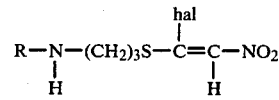

wherein hal represents a halogen atom and R containing up to twenty carbon atoms and being one of optionally substituted formyl, alkanoyl, alkenoyl, alkynoyl, benzoyl, carbamoyl, oxaloyl, alkoxycarbonyl, phenoxycarbonyl, phenalkoxycarbonyl, alkylthiocarbonyl, phenylthiocarbonyl, alkylthio-thiocarbonyl, phenylthio-thiocarbonyl, alkylsulfonyl, phenylsulfonyl, alkylaminosulfonyl, phenylaminosulfonyl, or phosphorus-containing acyl of the formula

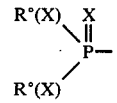

wherein each of R° independently is an optionally substituted alkyl or phenyl moiety, and each X independently is an oxygen or sulfur atom.

2. A compound according to claim 1 wherein R is alkanoyl containing 1 to 11 carbon atoms, haloalkanoyl containing 2 to 11 carbon atoms and 1 to 5 chlorine, fluorine and/or bromine atoms, phenylsulfonyl, alkylsulfonyl alkylsulfonyl containing 1 to 10 carbon atoms, (alkyl—O)$_2$P(O)— wherein each alkyl moiety contains 1 to 4 carbon atoms, (alkyl—O)$_2$P(S)— wherein each alkyl moiety contains 1 to 4 carbon atoms, (phenyl—O)$_2$P(O)—, dialkylcarbamoyl wherein each alkyl contains 1 to 4 carbon atoms, alkoxycarbonyl containing 2 to 11 carbon atoms, or alkylthiocarbonyl containing 2 to 11 carbon atoms, wherein each of these unsubstituted moieties can bear methyl, nitro, chlorine, fluorine or bromine as substituents.

3. A compound according to claim 2 wherein R is alkanoyl containing 1 to 11 carbon atoms, or haloalkanoyl containing 2 to 11 carbon atoms and 1 to 5 chlorine, fluorine and/or bromine atoms.

4. A compound according to claim 3 wherein R is alkanoyl containing 1 to 11 carbon atoms.

5. A compound according to claim 4 wherein R is formyl and hal is chlorine.

* * * * *